(12) United States Patent
Pitchford

(10) Patent No.: US 10,816,527 B2
(45) Date of Patent: Oct. 27, 2020

(54) TREE PRESERVATION MAPPING SYSTEM AND METHODS

(71) Applicant: Tree Matrix, Inc., Charlottesville, VA (US)

(72) Inventor: Keith Pitchford, Nellysford, VA (US)

(73) Assignee: Tree Matrix, Inc., Charlottesville, VA (US)

( * ) Notice: Subject to any disclaimer, the term of this patent is extended or adjusted under 35 U.S.C. 154(b) by 379 days.

(21) Appl. No.: 15/954,785

(22) Filed: Apr. 17, 2018

(65) Prior Publication Data

US 2018/0299420 A1 Oct. 18, 2018

Related U.S. Application Data

(60) Provisional application No. 62/486,767, filed on Apr. 18, 2017.

(51) Int. Cl.
*G01N 33/00* (2006.01)
*G06F 30/13* (2020.01)

(52) U.S. Cl.
CPC ......... *G01N 33/0098* (2013.01); *G06F 30/13* (2020.01)

(58) Field of Classification Search
None
See application file for complete search history.

(56) References Cited

U.S. PATENT DOCUMENTS

| | | | | |
|---|---|---|---|---|
| 6,145,244 | A * | 11/2000 | Hodko | A01B 47/00 210/602 |
| 9,007,256 | B1 * | 4/2015 | Ambusk | G01S 13/885 342/179 |
| 2004/0065012 | A1 * | 4/2004 | Byles | A01G 24/00 47/80 |
| 2004/0128909 | A1 * | 7/2004 | Smiley | A01G 29/00 47/58.1 SC |
| 2007/0289207 | A1 * | 12/2007 | May | A01G 9/16 47/17 |
| 2009/0280985 | A1 * | 11/2009 | Kostka | A01N 43/16 504/140 |
| 2015/0015697 | A1 * | 1/2015 | Redden | G01N 33/0098 348/89 |

* cited by examiner

*Primary Examiner* — Gregory J Toatley, Jr.
*Assistant Examiner* — Brandon J Becker
(74) *Attorney, Agent, or Firm* — K&L Gates LLP

(57) ABSTRACT

The present disclosure is directed to systems and methods for tree preservation efforts by determining a critical root zone of a selected tree within an existing landscape including hardscape elements. The critical root zones can be determined based upon the diameter size of each tree being impacted. The system includes generating a landscape map including visually representing the calculated critical root zone including any root zone loss within the existing landscape. In addition, the disclosure provides a system for determining survivability of an impacted tree that takes into account a number of factors to ensure a survivability percentage of at least 70%.

12 Claims, 2 Drawing Sheets

TREE PRESERVATION MAPPING SYSTEM AND METHODS

CROSS-REFERENCE TO RELATED APPLICATIONS

This application incorporates by reference and claims the benefit of priority to U.S. Provisional Application 62/486,767 filed on Apr. 18, 2017.

BACKGROUND OF THE INVENTION

The present disclosure relates to a tree preservation system to be used within a landscape architecture profession, and other related professions, to include, systems and methods for designing landscapes that promote tree sustainability and to predict tree survivability during construction. Growing large healthy trees is very difficult in urban and suburban areas and in order to successfully grow large trees they must be provided with sufficient space, high quality soil with adequate moisture, oxygen, and sufficient soil drainage. Adequate tree root growth provides for health and structural stability of trees in the landscape (such as any landscape or land development that is for cities, towns, villages, suburbs, or other areas for residential, commercial, or industrial use). Urban landscape, traffic of all types, land development infrastructure and other structures create heavily compacted soils that are not capable of adequately supporting developing growth of trees where the soil no longer is porous for tree growth. Growing trees becomes increasingly difficult as the area devoted to human needs increases, causing a decrease in the area that can be devoted to providing soil for trees. Attempts to solve the problem of reduced space have resulted in solutions that are expensive, only meet a portion of the goals, address limited volumes of soil and/or have high maintenance cost.

As urban and suburban areas become increasingly dense, open space is at a premium and it becomes increasingly difficult to find enough open space to grow trees. Commonly, trees are positioned in openings in the sidewalk. However, as the trees grow, the roots extend under the sidewalk and create conflict, making the sidewalk hazardous or unsightly. When this occurs, the tree and/or hardscape are usually removed.

The hardscape surfaces, defined here as load-bearing, generally impervious, surfaces, such as concrete sidewalks, parking lots, and driveways that are necessary for the convenience of humans are usually supported on compacted soil or fill. Trees and similar vegetation, on the other hand, require nutrients and water, and send forth an extensive root structure in search of these elements that are essential to growth of the tree. The structural root system is destructive to the hardscape surface over time, and the hardscape surfaces are also detrimental to the survivability of the tree. For example, the compacted soil beneath the hardscape stunts the growth of the root system and the growth of the tree.

Given that trees can account for 20% of a property value, not to mention their incalculable value to the local and broader environment, there are significant incentives for preservation and survivability. Since the cost of effective tree preservation is only a fraction of that twenty percent, there is every incentive to employ an effective, predictive and accurate method of preservation. This is not only because it is environmentally the right thing to do. It will reduce costs, reduce uncertainty and reduce the burden of blame and responsibility, which is the bane of developers, builders and regulators.

Accordingly, there is a need for systems and methodologies for selecting not only the specific tree type to include in a specific landscape. In addition, there is a need for a landscape planning system that includes the specific location to plant the tree for the survival of the tree, wherein the system and methods take into account the hardscape elements.

BRIEF SUMMARY OF THE INVENTION

The present disclosure is directed to systems and methods for tree preservation efforts by determining a critical root zone of a selected tree within an existing landscape including hardscape elements. The critical root zones can be determined based upon the diameter size of each tree being impacted. The system includes generating a landscape map including visually representing the calculated critical root zone within the existing landscape.

In addition, the disclosure provides a system for determining survivability of a specific tree based on a number of factors. For example, the system includes a formula based on five preservation factors that can be used to predict survivability of an impacted tree (or protected in place). Such systems and methods can be used for established trees that are already growing in a landscape and impacted by a disturbance to the ground around the tree, such as cutting roots, or compacting soil, among others. These events can stress trees, and can lead to their death. The survivability formula takes into account five factors to be considered when altering a landscape or otherwise disturbing the soil. The resulting survivability percentage is an expression of how likely it is that the tree will survive this stressful disturbance. A percentage of 70%, or greater, is considered to be a baseline for survivability.

The system can include a landscape planning tool that aids landscape designers in picking the "right plant, for the right location" from a database of plant characteristics including soil type, sun availability, rooting area, etc. A huge problem in landscape architecture and design is the tendency to put the wrong plant, in the wrong location.

An advantage of the present system includes assisting landscape professionals such as designers, architects, and contractors to install the right tree in the right place.

A further advantage of the present system is that the method aids professionals in selecting the best type of tree for the site being designed such that the selected tree has a high likelihood of survivability, resulting in less maintenance time and cost.

Another advantage of the present method involves calculating the survivability of an impacted tree in order to determine if the tree receives a survivability factor of greater than 70%.

Yet another advantage of the present system is taking into account the hardscape environment around the tree rooting areas, canopy growing space, sun availability, and soil composition.

Yet another advantage of the present system is to determine a realistic critical root zone within an existing landscape.

Another advantage is to quantifiably determine the percent chance of tree survival in construction, and other land development situations.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
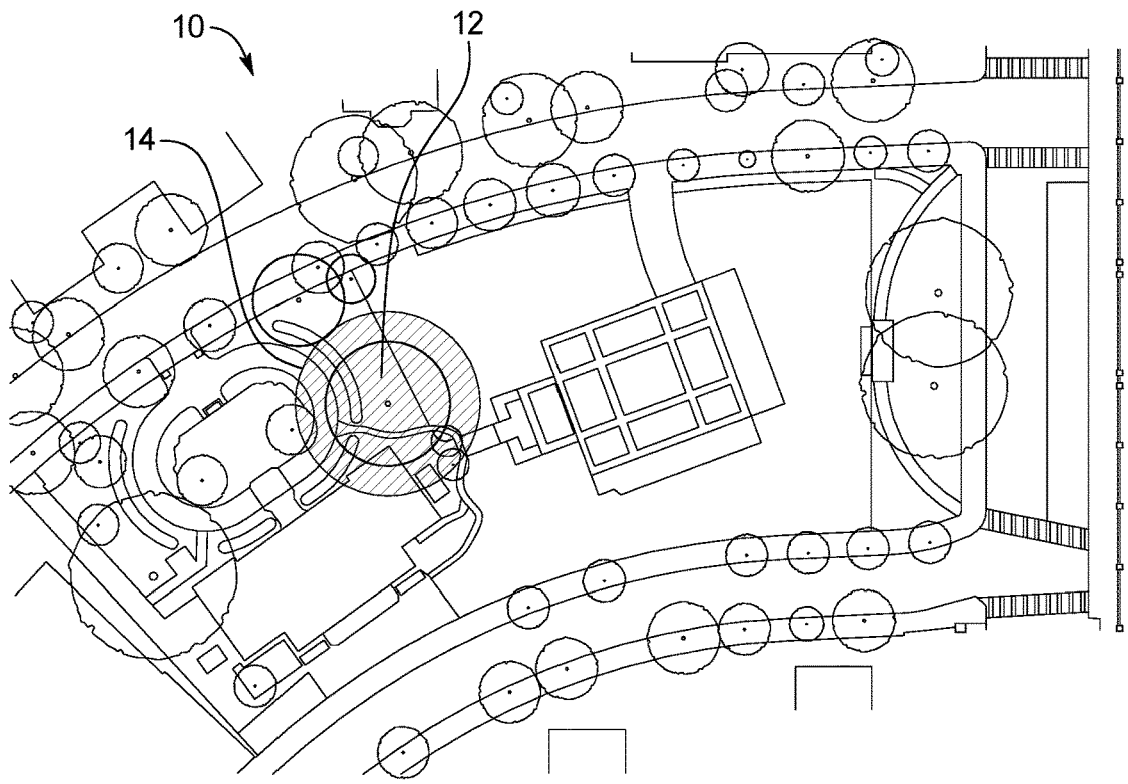
FIG. 1 is a schematic of an example of a residence that has an apartment complex planned.

The present disclosure is directed to systems and methods for tree preservation efforts by determining a critical root zone of a selected tree, wherein the system takes into account the hardscape elements within a landscape. The critical root zones can be determined based upon the diameter size of each tree being impacted. The system includes generating a landscape map including visually representing the calculated critical root zone. The system can use computer added design software or GIS software for generating the landscape map.

In most preservation landscape plans (e.g., maps), circles are drawn around trees to depict their critical root zone (CRZ). The industry standard for a critical root zone is the minimum volume of roots necessary for maintenance of tree health and stability. However, the conventional critical root zone determination does not provide information about the shape or direction of root growth. Circles are helpful in calculating the surface area of CRZ, yet they are not an accurate representation of the actual pattern of growth of tree roots. Because the circular surface area represented by the CRZ does not fully capture the shape, volume, and direction of root growth, relying solely on the CRZ for landscape design can often lead to tree loss. Tree roots grow along paths of least resistance, and into areas where roots can absorb water, air and nutrients. The resulting patterns might be circles, but such cases are rare.

Proper tree preservation planning relies on calculating the area of root zone necessary to support a tree after root loss. For the calculation of the root zone in the present method, the area of a circle, ($A=\pi r^2$) is used. However, in the present method the radius (r) is determined for trees up to 30 inches in diameter, wherein 1 foot is added of radial distance for every inch of diameter at breast height (DBH) (DBH, 4.5 feet above ground). For trees larger than 30 inches in diameter, 1.5 feet is added for every inch of diameter. The resulting calculated root zone accurately reflects the area that is necessary, especially for the younger more vigorous trees, and also for larger, mature trees.

After the root zone area is calculated, the realistic rooting pattern for each tree candidate is determined, as well as a map of the full extent of the CRZ. Landscape conditions can act to deflect root expansion, including hardscapes such as building foundations, retaining walls, curbing, and large impervious surfaces such as parking lots, driveways, etc. There may also be features that attract root expansion such as moist soil conditions, undisturbed soils or even a forest grove situation where advantageous growing conditions exist. Roots can expand to a distance of at least 2 to 3 times the limits of the dripline. The resulting map of the landscape with the calculated root zone areas is not necessarily perfect circles, but rather a collection of odd shapes that more accurately represent the real root zone dimensions taking the hardscape elements into account.

For example, FIG. 1 depicts a residence that has an apartment complex plan map 10. The existing beech 12 is 30 inches of diameter at breast height (DBH), and assumed to be in good condition. The CRZ 14 is shown as a circle, and based upon 1.5' for each inch of DBH. Based upon this depiction, the anticipated root loss from new work within the limits of disturbance (LOD) is 15% total. The LOD is the limits of construction activity, such as the area of root pruning or cutting. Typically, the LOD is determined by the construction company. The LOD will delineate where construction activity will stop, and root protection begins.

Figure 2:
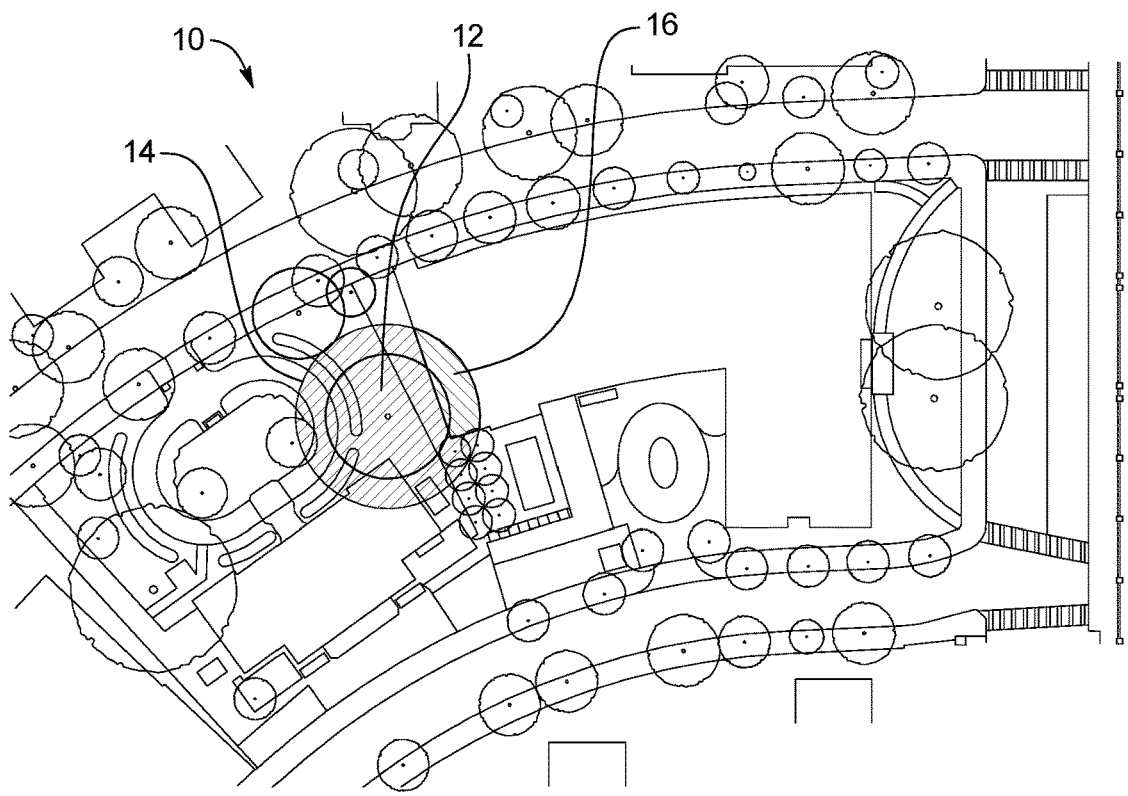
FIG. 2 depicts the critical root zone map circles using the conventional method, as well as the percentage of CRZ lost to construction.

FIG. 2 depicts the map 10 for the beech tree 12 of the critical root zone 14 using the conventional method—mainly calculating the CRZ wherein "r" is the radial distance of the diameter at breast height. The traditional method simply uses circles around each tree, with a radius calculated as either 1' per inch of trunk diameter, or 1.5' per inch of trunk diameter. However, the traditional method is often misleading because roots don't grow in circles most of the time. FIG. 2 illustrates the conventional method of using circles around trees, wherein the circles have a radial dimension of either 1 foot per diameter inch, or 1.5 feet per diameter inch, depending upon the tree size. The smaller circle illustrates the 1 foot for each 1 inch diameter circle would be, and the larger circle is the 1.5 feet for each 1 inch diameter circle. FIG. 2 illustrates how misleading the smaller dimension is in terms of potential root loss.

Figure 3:
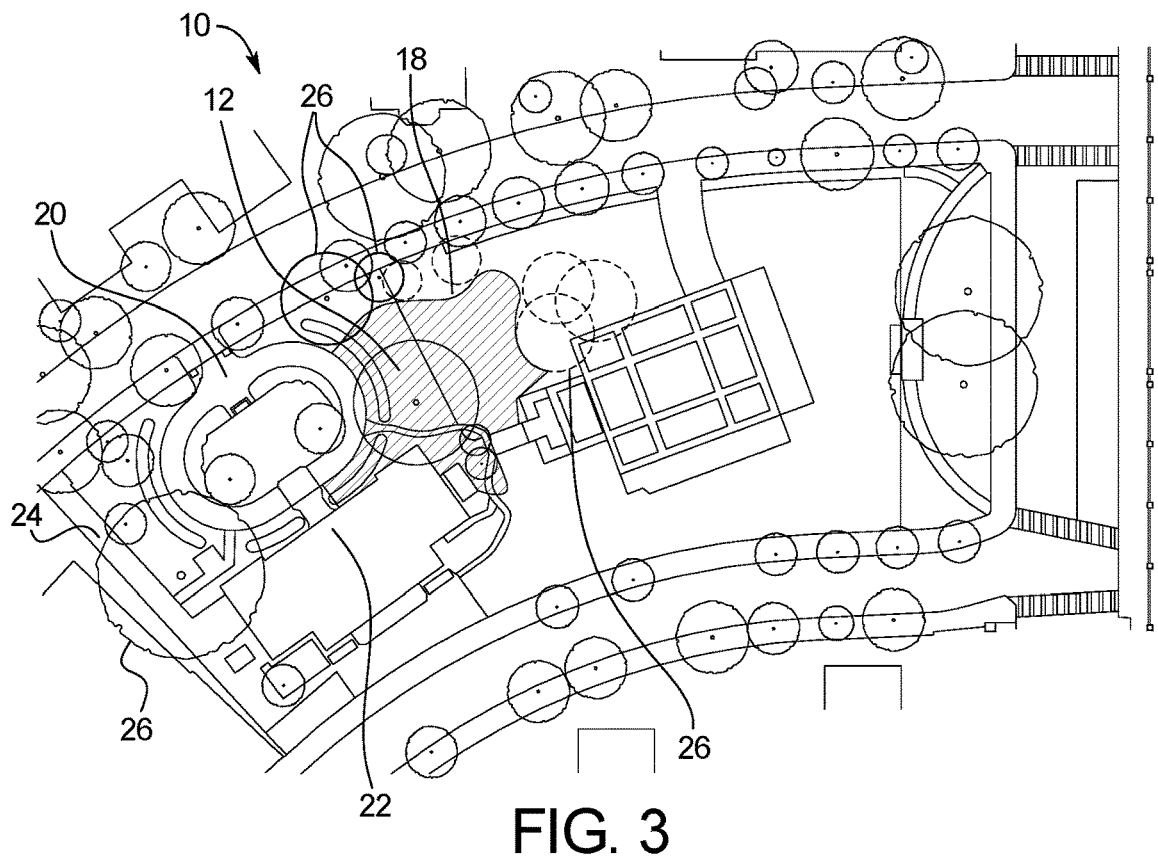
FIG. 3 depicts the critical root zone map illustrating the critical root zone map circles using the present method before construction based upon the square footage calculation of the CRZ circles.

In contrast, FIG. 3 illustrates the critical root zone map 10 including the critical root zone 18 calculated using the present method before construction for the beech tree 12. In contrast to the conventional method, the present method calculates the critical root zone area by using the formula $A=\pi r^2$ and takes into account any hardscape elements including, but not limited to, the driveway 20, house foundation 22, path 24, and competing tree roots 26 from the surrounding trees that may redirect root expansion. In other words, in an example, the present system overlays the circular critical root zone calculated onto the landscape map, and then manipulates the shape of the critical root zone to maintain the calculated area but changes the shape to account for the real rooting pattern and any hardscape that may deflect the roots.

In addition, the system can calculate the root loss by determining the difference between the area of the critical root zone and any area loss based on hardscape items. For example, if the area of the circle for a tree is 1200 square feet, but the 1200 square feet does not fit within the landscape, and 456 square feet has to be removed from the 1200 square feet (e.g., during construction), then such would result in a root loss 30 of 38%. Such calculation can be performed using CAD software. Therefore, when the present method CRZ's are drawn, and the LOD is considered, the extent of root loss is actually 38%. Therefore, instead of a conventional plan that appears to have minimal root loss, the impact would be significant in reality.

Figure 4:
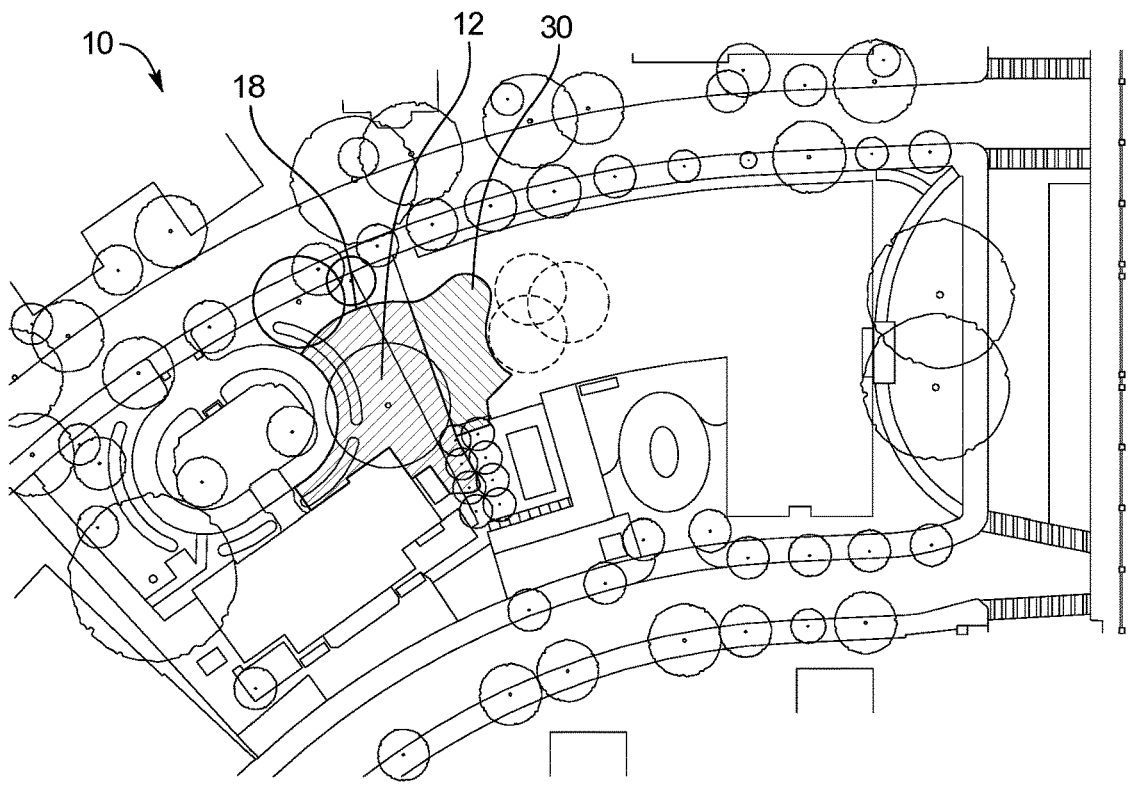
FIG. 4 depicts the critical root zone map illustrating the critical root zone map circles using the present method after construction, as well as the percentage of CRZ lost due to construction.

FIG. 4 illustrates the critical root zone map 10 including the critical root zone 18 and root loss zone 30 using the present method. The conventional method using merely circles greatly underestimates the percentage of roots being lost. The traditional circle method assumes that roots are in places where they will not be found, such as under buildings, or beyond large retaining walls. The conventional system assumes that the diagram does not extend further than roots can be expected from the tree, such as 2 to 3 times beyond the dripline. In contrast, mapping the critical root zone with CAD or GIS software can identify an area that is more realistic, and can show the entire CRZ calculated by the area of a circle formula, in addition to area loss by root loss due to construction or other hardscape elements.

Once the critical root zones are established using the method disclosed herein and with the option of integrating with Computer Added Design software, a new site plan can be overlaid on the critical root zones. FIG. 4 illustrates overlaying the footprint of the new building, or LOD, on top of the newly mapped root zone. The 38% loss is determined by calculating the area of that shape, and deducting that from the total area of the critical root zone that was calculated.

In addition, the disclosure provides a system for determining a survivability of a tree based on a number of factors. For example, the survivability of the tree can be determined based on climate, soil, season of impact, type of tree, number of impacted root quadrants, tree condition at the time of impact, and percentage of critical root zone lost.

The survivability percentage for an impacted tree can be based on numerous factors including, but not limited to, species tolerance to root loss, tree condition at the time of impact, critical root zone loss percentage, season of impact, and quadrants of CRZ impacted. The survivability percentage value can be determined to ensure selecting a tree of particular condition that can give rise to a survivability percentage of at least 70%.

Trees typically can be classified into three root loss tolerance categories: high, moderate, and low. Table 1 includes examples of trees in each category.

TABLE 1

| High tolerance | Moderate Tolerance | Low Tolerance |
| --- | --- | --- |
| Willow Oak | Hickory | Tulip Poplar |
| White Oak | Horsechestnut | Black Walnut |
| Silver Maple | Eastern Red Cedar | Sourwood |
| Boxelder | Dogwood | European Beech |
| Sycamore | Southern Magnolia | Cherries |
| American Elm | Eastern White Pine | Linden |
| Hackberry | Sugar Maple | Yellowwood |
| Pines | | |
| Black Locust | | |
| Red Maple | | |

Tree condition at the time of impact is categorized from excellent to very poor. Several reliable scales are available, including one published by the International Society of Arboriculture (ISA). Alternatively, a condition factor can be concluded from other sources or based upon visual inspection of growth rates, consistency of growth, percentage of live crown, live crown ratio, history of failure, structural defects and anticipated life span. Unfortunately, tree condition can be a subjective factor, but should not vary wildly if the assessor has adequate arboricultural experience.

Critical root zone loss 30 can be calculated using computer aided design software (CAD), which can map the CRZs and calculate the amount of root zone lost to disturbance. Not generally shown on preservation plans, but equally important is the dimension of the supporting roots within the "root plate" around each tree. It is very important to avoid severing these roots because damage to them can result in catastrophic windthrow failure. The root plate is the "base of the wine glass" around each tree that is responsible for structural support. To avoid damaging these large roots, the baseline formula of 6 inches of radial distance around the tree is used for each inch of trunk diameter at breast height.

Several formulas for determining the root plate are addressed in an article from Arborist News, June 2010. One of the more commonly used formulas is that the radial distance of these roots is about 6 inches for each inch of trunk diameter. For example, a 20 inch diameter tree would have a root plate with a radial dimension of 10 feet in radius; and, a 30 inch diameter tree would have a root plate of 15 feet in radius.

The season in which the tree is impacted also affects the survivability percentage of the tree. The least impactful season for severing roots is the dormant season because of the low energy demand for the tree during this time. Alternatively, the most stressful time are the spring months when energy demands are at their highest. Recovery time for trees impacted in the dormant season may only be one year, but if damaged during the spring, the recovery time can be 3 to 4 times this amount.

As shown in Table 2, if roots are severed during the fall season the anticipated recovery time is 2 years. If damage occurs during the summer months (June-August), the anticipated lag time is 3 years. If inflicted in the spring (e.g., March-May), the lag time is 4 years. Such information suggests that the most harmful time of year to cut roots is during the spring months when the tree's energy demands are the highest.

TABLE 2

| Season | Energy Needs | Recovery Time |
| --- | --- | --- |
| Winter | Low | 1 year |
| Spring | High | 4 years |
| Summer | Medium-High | 3 years |
| Fall | Medium-Low | 2 years |

The number of quadrants, or "sides," of the root zone impacted can also have a significant impact on the survivability of the impacted tree. Damaging just one quadrant has little impact, however, the consequences become more severe with each additional quadrant impacted. In fact, impacting three or four sides can be not only incrementally stressful, but exponentially stressful to the impacted tree.

It is not unusual to find trees in situations where there are just two, or three sides to their root system. A classic example is street trees where one side is restricted by a hardscape element such as a road, leaving functional roots on only three sides, including the area within a continuous grass strip on two sides, and perhaps another under the sidewalk as the roots expand toward a nearby lawn area. Or, there may be only two sides to some street trees if it is growing in a long, continuous strip with no access to other rooting areas, or in an elevated planter that is so common in parking lots.

The survivability percentage of an impacted tree can be calculated based on values for each factor that contributes to tree survivability including, but not limited to, species tolerance to root loss, tree condition at the time of impact, critical root zone loss percentage, season of impact, and quadrants of CRZ impacted. The values of each factor are discussed below.

Tolerance to root loss: High can be associated with 6x points; Moderate can be associated with 3x points; and Low can associated with x points, wherein x can be an integer.

CRZ loss percentage: less than 25% can be associated with 4x points; 25-30% can be associated with 3x points; 31-40% can be associated with 2x points; 41-50% can be associated with x points; and greater than 50% can be s associated with 0 points, wherein x can be an integer.

Tree Condition: Excellent can be associated with 4x points; Good can be associated with 3x points; Good/Fair can be associated with 2x points; Fair is associated with x points; and Poor can be associated with 0 points, wherein x can be an integer.

Season of Impact: Dormant (November-February) can be associated with 5x points; Fall (September-October) can be associated with 3x points; Summer (June-August) can be associated with 2x points; and Spring (March-May) can be associated with 0 points, wherein x can be an integer.

CRZ quadrants impacted: 1 Quadrant (1/4) can be Associated with 6x points; 2 quadrants (2/4, 1/3) can be associated with 3x points; 3 quadrants (3/4, 2/3, ½) can be associated with x points; and 4 quadrants (4/4, 3/3, 2/2) can be associated with 0 points, wherein x can be an integer.

In the present method, a score of one hundred points is the highest possible score. Typically, the resulting survivability percentage of 70% or more indicates a good preservation candidate.

The final component of any tree preservation program can be aftercare. However, because aftercare is so infrequently and inappropriately applied, aftercare is typically not considered an equally weighted factor. But if aftercare is provided for at least 3-5 years following injury, or for the recovery period described above, the survivability percentage is increased by 10%.

Therefore, aftercare is important because it may be the difference between a tree surviving or not, and in the end can save trees that add upwards of 20% of a property's value. Aftercare can include, but not be limited to, a supplemental irrigation system, insect control, and disease control.

Four of the five factors can be adjusted to increase the chances of survivability, including expanding the CRZ, altering the timing of root pruning, improving the condition of the tree prior to root damage, and limiting the number of CRZ quadrants impacted. The objective should be able to create a preservation map plan where the survivability percentages will be 70%, or greater, for each candidate.

The survivability percentage value can be used to assist landscape professionals such as designers, architects, and contractors. Therefore, the present method aids professionals in selecting the best type of tree for the site being designed such that the selected tree has a high likelihood of survivability, resulting in less maintenance time and cost.

Examples

In a specific example, the following values of variables can be used in the calculation of survivability. However, the disclosure is not limited to the exact values given in the examples. Any relative suitable values can be used.

Tolerance to root loss: High is associated with 24 points; Moderate is associated with 12 points; and Low is associated with 4 points.

CRZ loss percentage: less than 25% is associated with 16 points; 25-30% is associated with 12 points; 31-40% is associated with 8 points; 41-50% is associated with 4 points; and greater than 50% is associated with 0 points.

Tree Condition: Excellent is associated with 16 points; Good is associated with 12 points; Good/Fair is associated with 8 points; Fair is associated with 4 points; and Poor is associated with 0 points.

Season of Impact: Dormant (November-February) is associated with 20 points; Fall (September-October) is associated with 12 points; Summer (June-August) is associated with 8 points; and Spring (March-May) is associated with 0 points.

CRZ quadrants impacted: 1 quadrant (1/4) is associated with 24 points; 2 quadrants (2/4, 1/3) is associated with 12 points; 3 quadrants (3/4, 2/3, ½) is associated with 4 points; and 4 quadrants (4/4, 3/3, 2/2) is associated with 0 points.

Example 1

A white oak with High tolerance, 28% root loss, Good condition, root pruned in December, and 1 of 4 quadrants has a resulting survivability value of 92%, which is calculated using the values above (24+12+12+20+24=92%).

Example 2

A tulip poplar with Low tolerance, root loss, Good/Fair condition, root pruned in June, and 2 of 4 quadrants impacted has a resulting survivability value of 40%, which was calculated using the above values (4+8+8+8+12=40%).

Example 3

A pignut hickory with Moderate tolerance, 34% root loss, Fair condition, root pruned in December, and 1 of 4 quadrants impacted results in a survival percentage value of 68%, which was calculated using the above values (12+8+4+20+24=68%).

Example 4

An eastern white pine with a Moderate tolerance, 23% root loss, Good condition, root pruned in May, 1 of 3 quadrant impacted results in a survivability percentage value of 52%, which was calculated using the above values (12+16+12+0+12=52%).

Example 5

A black walnut with a Low tolerance, 24% root loss, Good/Fair condition, root pruned in July, 2 of 3 quadrants impacted results in a survival percentage value of 40%, which was calculated using the above values (4+16+8+8+4=40%).

Example 6

A Norway spruce with a High tolerance, 40% root loss, Good condition, root pruned in May, 4 of 4 quadrants impacted results in a survival percentage value of 44%, which was calculated using the above values (24+8+12+0+0=44%).

Aspects of the systems and methods described herein are controlled by one or more controllers. The one or more controllers may be adapted to run a variety of application programs, access and store data, including accessing and storing data in the associated databases, and enable one or more interactions as described herein. Typically, the controller is implemented by one or more programmable data processing devices. The hardware elements, operating systems, and programming languages of such devices are conventional in nature, and it is presumed that those skilled in the art are adequately familiar therewith.

For example, the one or more controllers may be a PC based implementation of a central control processing system utilizing a central processing unit (CPU), memory and an interconnect bus. The CPU may contain a single microprocessor, or it may contain a plurality of microprocessors for configuring the CPU as a multi-processor system. The memory may include a main memory, such as a dynamic random-access memory (DRAM) and cache, as well as a read only memory, such as a PROM, EPROM, FLASH-EPROM, or the like. The system may also include any form of volatile or non-volatile memory. In operation, the memory stores at least portions of instructions for execution by the CPU and data for processing in accord with the executed instructions.

The one or more controllers may also include one or more input/output interfaces for communications with one or more processing systems. Although not shown, one or more such interfaces may enable communications via a network, e.g., to enable sending and receiving instructions electronically. The communication links may be wired or wireless.

The one or more controllers may further include appropriate input/output ports for interconnection with one or more output mechanisms (e.g., monitors, printers, touchscreens, motion-sensing input devices, etc.) and one or more input mechanisms (e.g., keyboards, mice, voice, touchscreens, bioelectric devices, magnetic readers, RFID readers, barcode readers, motion-sensing input devices, etc.) serving as one or more user interfaces for the controller. For example, the one or more controllers may include a graphics subsystem to drive the output mechanism. The links of the peripherals to the system may be wired connections or use wireless communications.

Although summarized above as a PC-type implementation, those skilled in the art will recognize that the one or more controllers also encompasses systems such as host computers, servers, workstations, network terminals, and the like. Further one or more controllers may be embodied in a device, such as a mobile electronic device, like a smartphone or tablet computer. In fact, the use of the term controller is intended to represent a broad category of components that are well known in the art.

Hence aspects of the systems and methods provided herein encompass hardware and software for controlling the relevant functions. Software may take the form of code or executable instructions for causing a controller or other programmable equipment to perform the relevant steps, where the code or instructions are carried by or otherwise embodied in a medium readable by the controller or other machine. Instructions or code for implementing such operations may be in the form of computer instruction in any form (e.g., source code, object code, interpreted code, etc.) stored in or carried by any tangible readable medium.

As used herein, terms such as computer or machine "readable medium" refer to any medium that participates in providing instructions to a processor for execution. Such a medium may take many forms. Non-volatile storage media include, for example, optical or magnetic disks, such as any of the storage devices in any computer(s) shown in the drawings. Volatile storage media include dynamic memory, such as the memory of such a computer platform. Common forms of computer-readable media therefore include for example: a floppy disk, a flexible disk, hard disk, magnetic tape, any other magnetic medium, a CD-ROM, DVD, any other optical medium, punch cards paper tape, any other physical medium with patterns of holes, a RAM, a PROM and EPROM, a FLASH-EPROM, any other memory chip or cartridge, or any other medium from which a controller can read programming code and/or data. Many of these forms of computer readable media may be involved in carrying one or more sequences of one or more instructions to a processor for execution.

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims.

The invention claimed is:

1. A system for generating a critical root zone map for an impacted tree within a landscape, wherein the landscape includes a maximum area for the impacted tree;
wherein the system comprises:
a controller;
a memory coupled to the controller, wherein the memory is configured to store program instructions executable by the controller;
wherein in response to executing the program instructions, the controller is configured to:
receive a trunk diameter at breast height associated with the impacted tree;
determine a critical root zone area based on a trunk diameter at breast;
determine a critical root zone loss percentage based the critical root zone area and the maximum area of the impacted tree in the landscape;
generate a critical root zone map, wherein the critical root zone map visually illustrates the area of the critical root zone area and the critical root zone loss percentage within the landscape; and
visually display the critical root zone map on a user interface in communication with the controller.

2. The system of claim 1, wherein the root plate area is calculated by multiplying the trunk diameter at breast height by six inches.

3. The system of claim 1, wherein if the impacted tree has a diameter of 30 inches or less, the critical root zone is calculated by $A=\pi r^2$ wherein "r" is determined by adding 1 foot for every inch of diameter at breast height of the impacted tree.

4. The system of claim 1, wherein if the impacted tree has a diameter of greater than 30 inches, the critical root zone is calculated by $A=\pi r^2$ wherein "r" is determined by adding 1.5 feet for every inch of diameter at breast height of the impacted tree.

5. The system of claim 1, wherein the controller is further configured to manipulate the shape of the critical root zone area within the landscape while maintaining the calculated area of the critical root zone area.

6. The system of claim 1, wherein the shape of the critical root zone area is not circular.

7. A system for generating a survivability percentage for an impacted tree within a landscape, wherein the system comprises:
a controller;
a memory coupled to the controller, wherein the memory is configured to store program instructions executable by the controller;
wherein in response to executing the program instructions, the controller is configured to:
receive a tree type of the impacted tree;
determine a tolerance category selected from High tolerance, Moderate tolerance, and low tolerance based on the tree breed;
receive a tree condition at the time of impact, wherein the tree condition is selected from Poor condition, Fair condition, and Good condition;
receive a season of impact, wherein the season of impact is selected from winter, spring, summer, and fall;
receive the number of root zone quadrants impacted;
receive a critical root zone loss percentage;
determine a survivability percentage based on the tolerance category, the tree condition at the time of impact, the critical root zone loss percentage, the season of impact, and the number of root zone quadrants impacted; and
visually display the survivability percentage on the critical root zone map on a user interface in communication with the controller.

8. The system of claim 7, wherein the tree tolerance of High is associated with 6x points, wherein the tree tolerance of Moderate is associated with 3x points, and wherein the tree tolerance of Low is associated with x points, wherein x is an integer.

9. The system of claim 7, wherein the critical root zone loss percentage of less than 25% is associated with 3x points, wherein the critical root zone loss percentage of 31-40% is be associated with 2x points, wherein the critical root zone loss percentage of 41-50% is be associated with x points, and wherein the critical root zone loss percentage of greater than 50% is associated with 0 points, wherein x is an integer.

10. The system of claim 7, wherein the tree condition at the time of impact of Excellent is associated with 4x points, wherein the tree condition at the time of impact of Good is associated with 3x points, wherein the tree condition at the time of impact of Good/Fair is associated with 2x points, wherein the tree condition at the time of impact of Fair is associated with x points, and wherein the tree condition at the time of impact of Poor can be associated with 0 points, wherein x is an integer.

11. The system of claim 7, wherein the season of impact of November through February is associated with 5x points, wherein the season of impact of September through October is associated with 3x points, wherein the season of impact of June through August is associated with 2x points, and wherein the season of impact of March through May is associated with 0 points, wherein x is an integer.

12. The system of claim 7, wherein the critical root zone quadrants impacted of 1 quadrant is associated with 6x points, wherein the critical root zone quadrants impacted of 2 quadrants is associated with 3x points, wherein the critical root zone quadrants impacted of 3 quadrants is associated with x points, and wherein the critical root zone quadrants impacted of 4 quadrants is associated with 0 points, wherein x is an integer.

* * * * *